(12) United States Patent
Chung

(10) Patent No.: US 9,005,172 B2
(45) Date of Patent: Apr. 14, 2015

(54) HEMOSTASIS VALVE DEVICE

(71) Applicant: HUBIOMED Co., Ltd., Seoul (KR)

(72) Inventor: Sun Chung, Seongnam-si (KR)

(73) Assignee: HUBIOMED Co., Ltd., Seoul (KR)

( * ) Notice: Subject to any disclaimer, the term of this patent is extended or adjusted under 35 U.S.C. 154(b) by 0 days.

(21) Appl. No.: 14/070,508

(22) Filed: Nov. 2, 2013

(65) Prior Publication Data

US 2014/0194831 A1    Jul. 10, 2014

(30) Foreign Application Priority Data

Jan. 4, 2013    (KR) .................. 10-2013-0001201

(51) Int. Cl.
*A61M 39/06* (2006.01)
(52) U.S. Cl.
CPC ................................ *A61M 39/0613* (2013.01)
(58) Field of Classification Search
USPC ............. 604/164.01–164.02, 167.01–167.03,
604/167.05–167.06, 236, 246, 248, 256,
604/284, 533; 137/606; 251/149.1, 352;
600/208, 435
See application file for complete search history.

(56) References Cited

U.S. PATENT DOCUMENTS

| 5,405,330 | A  | * | 4/1995  | Zunitch et al. ................ 604/240 |
| 5,693,025 | A  | * | 12/1997 | Stevens .................... 604/167.03 |
| 7,628,783 | B2 | * | 12/2009 | McDaniel ...................... 604/533 |
| 8,262,622 | B2 | * | 9/2012  | Gonzales et al. ......... 604/167.01 |
| 2005/0154372 | A1 | * | 7/2005 | Minezaki ...................... 604/533 |
| 2010/0036329 | A1 | * | 2/2010 | Razack ......................... 604/256 |
| 2011/0054405 | A1 | * | 3/2011 | Whiting et al. .......... 604/167.03 |

FOREIGN PATENT DOCUMENTS

| KR | 10-2001-0022303 A | 3/2001 |
| WO |       99/06099 A2 | 2/1999 |

* cited by examiner

*Primary Examiner* — Theodore Stigell
*Assistant Examiner* — Amber Stiles
(74) *Attorney, Agent, or Firm* — LRK Patent Law Firm

(57) ABSTRACT

The present invention relates to a hemostasis valve device which allows a wire or a catheter to be inserted into the left or right coronary artery via the femoral artery or an arm artery when a Cardiac Catheterization or Percutaneous Transluminal Coronary Angioplasty operation is performed, wherein two independent sealing members are opened and closed by press and release actions of push buttons coupled to a body and the rotation of a fastening tube, respectively, so that the leakage of blood or the inflow of outside air is simply and effectively blocked during the operation, and a drug influx tube for allowing a medicine such as a thrombolitic drug to flow into a patient during the operation pivots and is adjusted in a stepwise manner within a certain range of angles according to body conditions or movements of the patient.

3 Claims, 6 Drawing Sheets

HEMOSTASIS VALVE DEVICE

BACKGROUND OF THE INVENTION

1. Technical Field

The present invention relates to a hemostasis valve device, especially to a hemostasis valve device which allows a tube, a guide wire, or a catheter to be inserted into the left or right coronary artery via the femoral artery or an arm artery at the time of a Cardiac Catheterization or Percutaneous Transluminal Coronary Angioplasty (PTCA) operation, wherein sealing members mounted in two independent positions are opened and closed by means of press and release actions of push buttons coupled to a fastening tube as well as the rotation of the fastening tube, respectively, so that the leakage of blood or the inflow of outside air is simply and clearly shut off during the operation, and a drug influx tube for allowing a medicine such as a thrombolitic drug to flow into a patient during the surgical operation pivots and is adjusted in a stepwise manner within a certain range of angles on a basis of body conditions or movements of the patient, so that the convenience and efficiency of the surgical operation is more improved.

2. Description of the Related Art

Surgical operation methods are tried that perform a variety of surgical procedures by artificially introducing an insertion device into a human body, for example, arteries, veins, the abdominal cavity, or other cavities.

A typical example of the above-mentioned methods is Cardiac Catheterization which is a nonsurgical method that does not open the chest of a patient and is performed when it is estimated that the patient has symptoms such as a chest pain, a faint, a difficulty in breathing, and the like caused by a coronary artery disease, wherein a needle hole is made on the radial artery in an arm or the femoral artery of a leg so that an insertion tube is inserted, and then a long narrow tube is located at an inlet of the coronary artery that is a blood vessel for supplying blood to the heart, and after that, a contrast medium is inserted into the coronary artery so that radiography is performed, and therefore, the degree by which the blood vessel is blocked as well as shapes and problems of the blood vessel are determined.

In addition, another nonsurgical method that does not open the chest of a patient is Percutaneous Transluminal Coronary Angioplasty (PTCA) which is performed when the patient is diagnosed that the cavity of the coronary artery diseasedly becomes narrower and it is impossible to cure the patient with drugs, wherein a medical device such as a catheter, a guide wire, a balloon, and a stent are inserted into the narrower coronary artery via a percutaneous artery, so that the narrower coronary artery is expanded. FIG. 6 illustrates an image showing a surgical method of PTCA or cardiac catheterization.

Besides, an additional hemostasis valve is typically applied to introduce a tube, a guide wire, or a catheter into a blood vessel at the time of the PTCA or cardiac catheterization operation, and more specifically, the hemostasis valve has functions for guiding the tube, guide wire, or catheter to be precisely inserted into a percutaneous artery or a vein, shutting off the leakage of blood that flows backward in the percutaneous artery or the vein during the surgical operation, preventing outside air from flowing into the blood vessel, and allowing a medicine such as a thrombolitic drug to be injected into the blood vessel if necessary.

As a prior art of the above-mentioned hemostasis valve, Korean Publication Number 1020010022303, entitled "medical fluid flow control valve" is disclosed.

The prior art of the Publication Number 1020010022303 has the technical characteristic that a sealing unit which has a disk shape and is made out of a thermoplastic styrene elastomer with low durometer values (hardness lower than shore A) such as a styrene ethylene butylene styrene block copolymer is properly included in a valve body and is compressively configured between a valve seat in the valve body and a cap connected to the valve body, wherein the sealing unit has one or more holes closed by the compression, the compression provides the sealing unit with a basal or upstream concave surface, and the sealing unit is highly endurable against the repeated removal as well as turning around while in operation of an insertion unit passing through a valve.

However, the medical fluid flow control valve of the prior art has disadvantages that the valve is inconveniently used because being configured in such a way that the sealing unit is compressed and decompressed according to the rotational movement of the cap, blood flowing backward during a surgical operation may easily leak because the sealing unit is mounted in one position, and improper outside air may flow into a blood vessel at the insertion of a tube, a guide wire, or a catheter (hereinafter, the tube, guide wire, and catheter are referred to as "different catheters"), which causes air embolism.

In addition, the valve of the prior art has another disadvantage that is inconveniently used because a drug influx tube for allowing a medicine such as a thrombolitic drug to be injected into a blood vessel as necessary during the surgical operation may not be variably adjusted on a basis of body conditions or movements of a patient and is fixedly formed outside an insertion tube configuring the control valve.

SUMMARY OF THE INVENTION

The present invention is applied to solve the disadvantages of the prior art, and an objective of the present invention is to provide a new hemostasis valve device which allows a tube, a guide wire, or a catheter to be inserted into the left or right coronary artery via the femoral artery or an arm artery at the time of a Cardiac Catheterization or Percutaneous Transluminal Coronary Angioplasty operation, wherein sealing members mounted in two independent positions are opened and closed by means of press and release actions of push buttons coupled to the outside of a fastening tube as well as the rotation of the fastening tube, respectively, so that the leakage of blood or the inflow of outside air is simply and effectively shut off during the surgical operation.

Another objective of the present invention is to provide a new hemostasis valve device in which a drug influx tube for allowing a medicine such as a thrombolitic drug to flow into a patient during the Cardiac Catheterization or PTCA operation pivots and is adjusted in a stepwise manner within a certain range of angles on a basis of body conditions or movements of the patient, so that the convenience of the surgical operation is more improved.

The objectives are achieved by the present invention configured to include: an insertion tube which has a guide hole into which a wire or a catheter is inserted along a longitudinal central axis formed inside in a penetrating manner, has a hose connector connected to a hose into which different catheters are inserted coupled to the lower portion, and has a threaded portion formed on the outer circumference of the upper portion; an elastic first sealing member which is inserted into and seated in the upper portion of the insertion tube, and has a through hole formed along a longitudinal central axis; a fastening tube which has an introduction hole inserted into the upper portion of the insertion tube along a longitudinal central axis formed inside, has a protrusion with an extended diameter formed at the upper portion of the introduction hole, has a spring receiver formed on the outer circumference of the introduction hole, and has another threaded portion engaging with the threaded portion, which is formed on the outer circumference of the upper portion of the insertion tube, formed on the inner circumference of the spring receiver; an elastic second sealing member which is inserted into and seated on the protrusion formed in the upper portion of the fastening tube, and has an incision hole in a circular or "+" shape formed on the top; a spring which is inserted into the spring receiver formed on the outer circumference of the fastening tube, and performs an elastic action according whether an external force is applied; a pressurizing piece which has a pressurizing hole formed in the center of the top in a projecting manner in order to maintain a state in which the hole adheres to the circumference of the incision hole in a circular or "+" shape on the second sealing member, has inclined planes formed on an edge of the upper portion in an outwardly opening manner, and is mounted in a state in which an edge of the lower end adheres to the upper end of the spring all the time; push buttons which are mounted on opposing sides of the pressurizing piece, and upwardly slide along the inclined planes on the pressurizing piece so as to press the pressurizing piece downwardly when a user pushes the buttons in a state in which tapered surfaces having the same slope as the inclined planes on the pressurizing piece are formed on the inner circumference of the upper portion of the buttons; a body which allows the push buttons to be inserted into and coupled to the body, and has another through hole communicating with the pressurizing hole on the pressurizing piece formed in the center; a pivot guiding piece which is formed in the middle of the insertion tube in an outwardly projecting manner and a disk shape, has a saw-toothed portion formed on the outer circumference within a certain range of angles, and has a drug guide hole, which communicates with the guide hole in the insertion tube, formed inside; and a pivot adjusting piece which is coupled to the outside of the pivot guiding piece in a covering manner, has another saw-toothed portion formed on the inner circumference corresponding to the saw-toothed portion on the pivot guiding piece, and has a drug influx tube formed in a position corresponding to the drug guide hole on the pivot guiding piece.

According to the present invention, the drug guide hole on the pivot guide piece is characterized in that the one opening far from the insertion tube is formed to be wider, while the other opening close to the insertion tube is formed to be narrower in order to correspond to the range of pivoting movement of the drug influx tube on the pivot adjusting piece.

DETAILED DESCRIPTION

Hereinafter, a preferred embodiment of the present invention is described in more detail with reference to the accompanying drawings.

Figure 1:
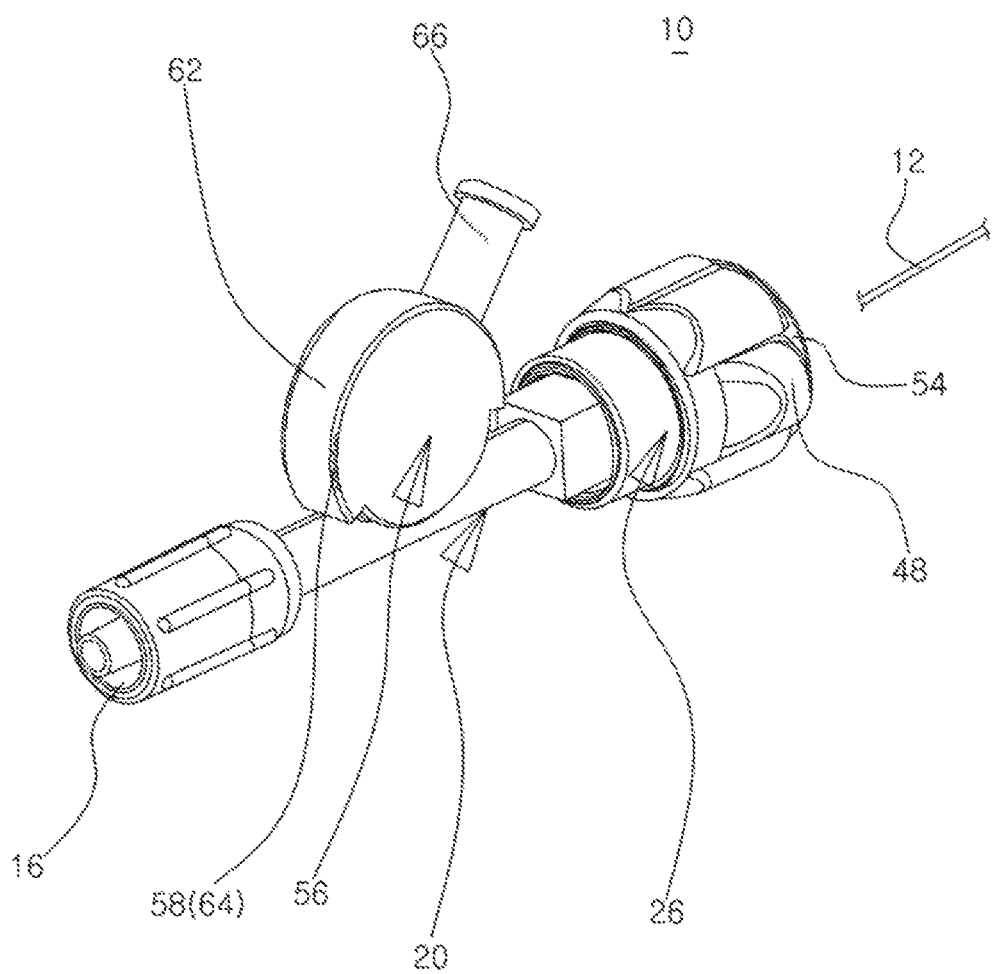
FIG. 1 illustrates a hemostasis valve device according to the present invention in a perspective view.
Figure 2:
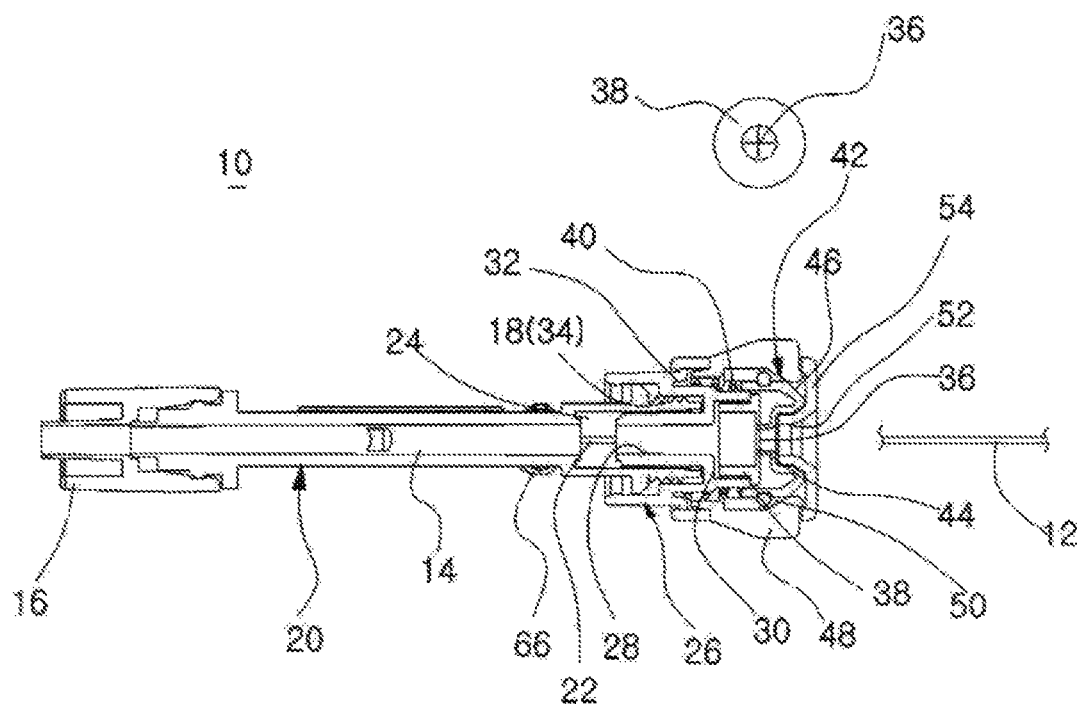
FIG. 2 illustrates a structure in which a first sealing member and a second sealing member are opened and closed in the hemostasis valve device according to the present invention in a cross sectional view.
Figure 3:
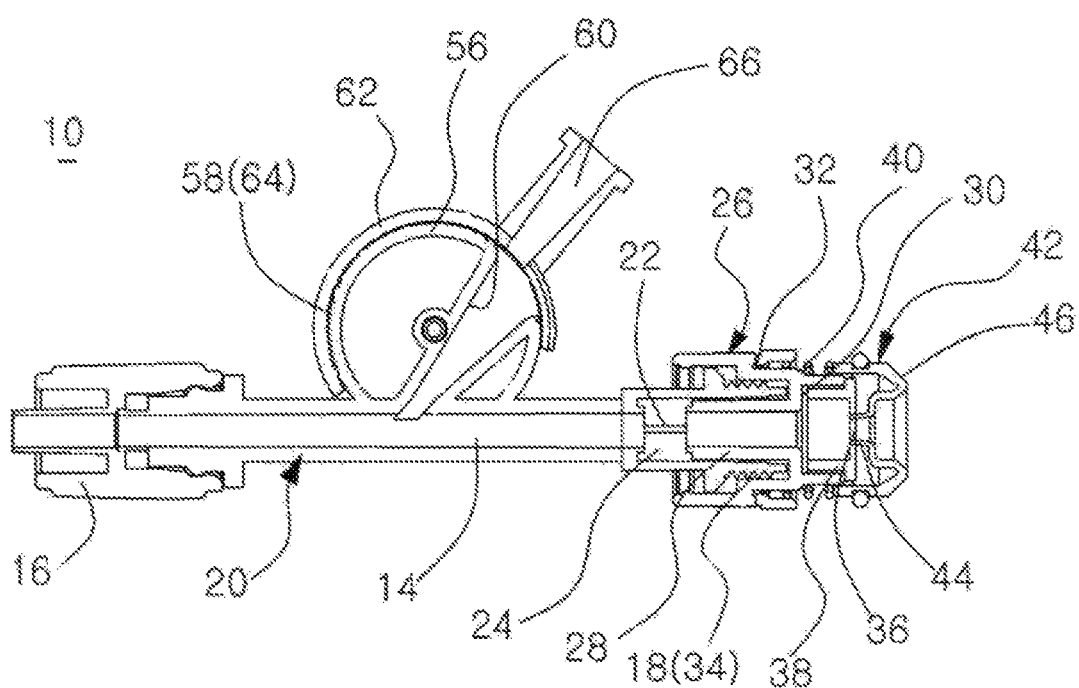
FIG. 3 illustrates a structure of a drug influx tube in the hemostasis valve device according to the present invention in a cross sectional view.
Figure 4:
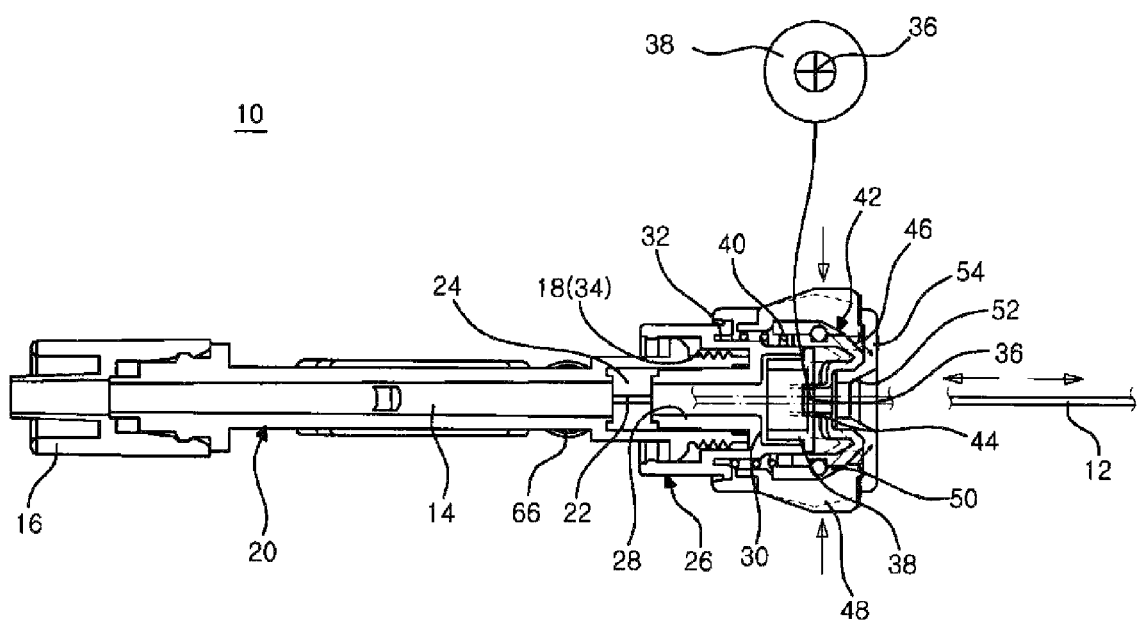
FIG. 4 illustrates opening and closing actions of the first and second sealing members according to the present invention in a cross sectional view.
Figure 5:
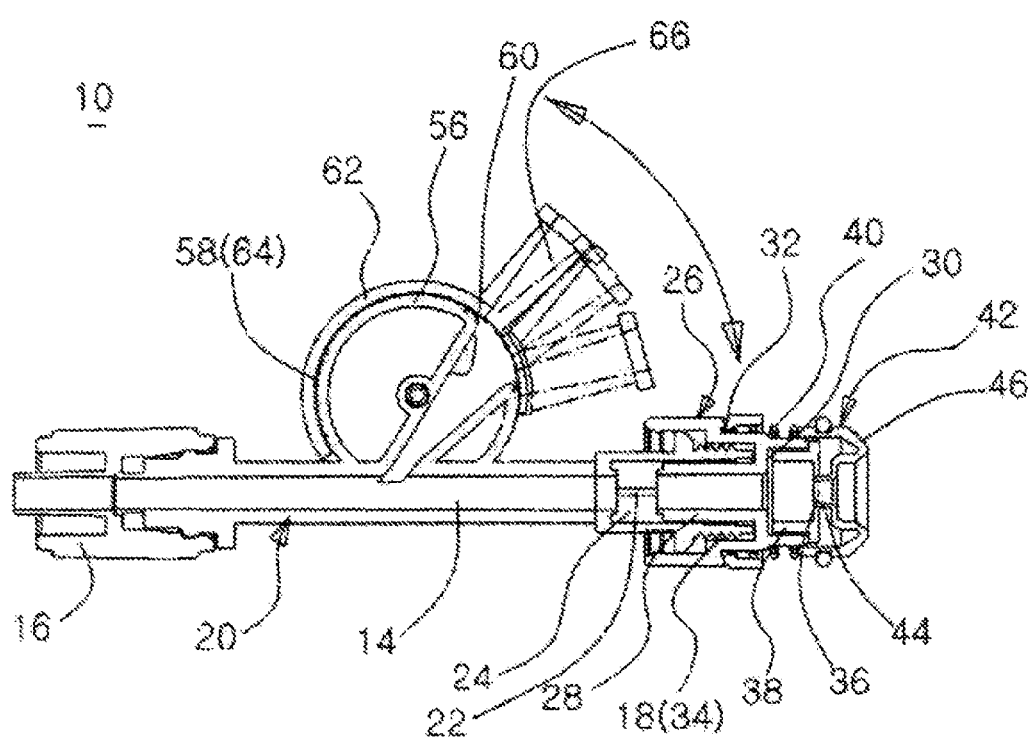
FIG. 5 illustrates an operation state of the drug influx tube according to the present invention in a cross sectional view.
Figure 6:
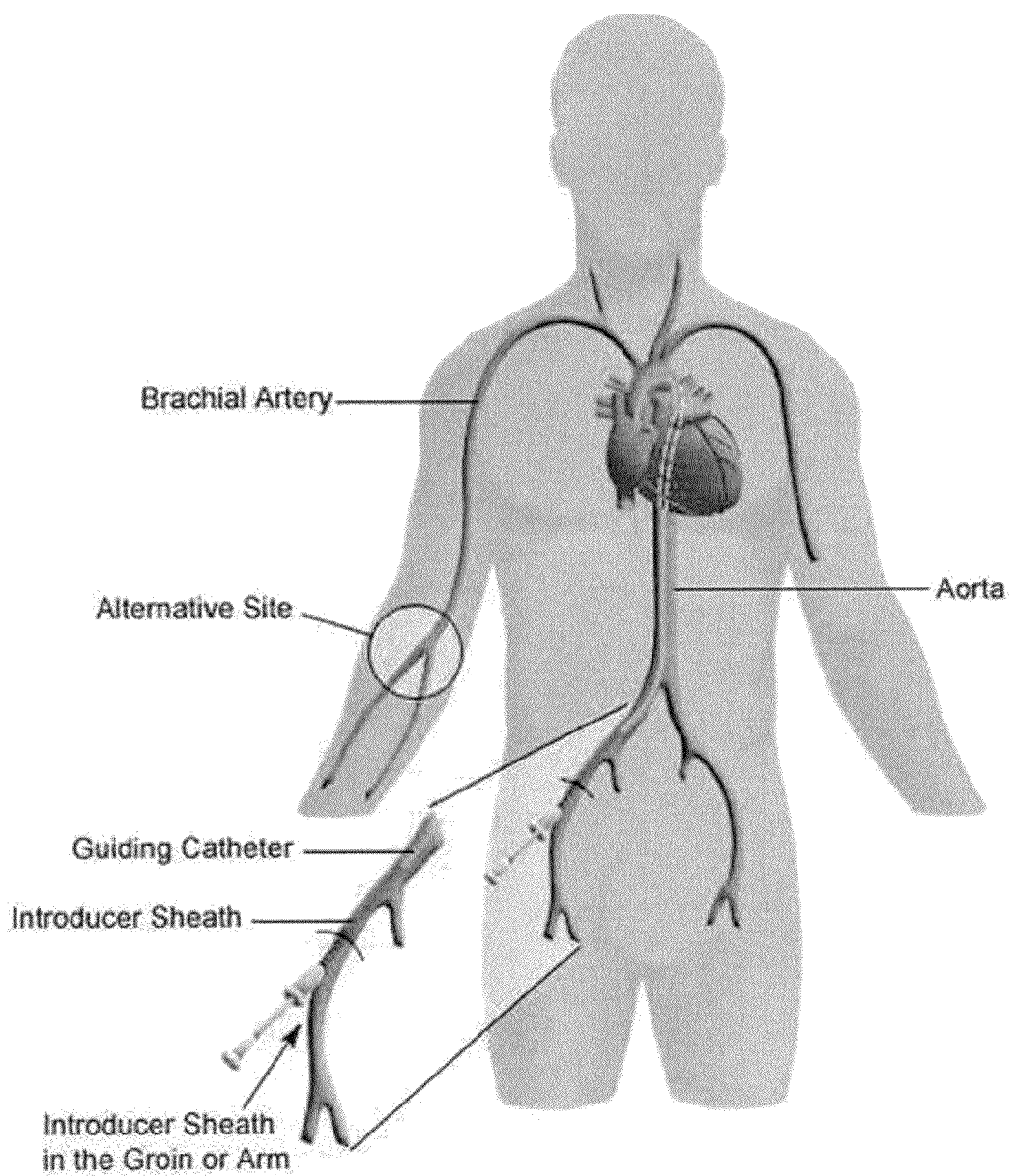
FIG. 6 illustrates an image showing a surgical method of PTCA or cardiac catheterization.

Referring to FIGS. 1 through 3, a hemostasis valve device 10 according to the present invention is provided with an insertion tube 20 which has a guide hole 14 into which different catheters 12 such as a tube, a wire, a catheter and the like are inserted along a longitudinal central axis formed in a penetrating manner, a hose connector 16 connected to a hose into which the different catheters 12 are inserted coupled to the lower portion, and a threaded portion 18 formed on the outer circumference of the upper portion.

According to the present invention, a first sealing member 24 is configured to be inserted into and seated in the upper portion of the insertion tube 20, have a through hole 22 formed along a longitudinal central axis, and have elasticity.

The insertion tube 20 additionally has a fastening tube 26 coupled to the upper portion in a thread-engaging manner, wherein the fastening tube 26 is configured to have an introduction hole 28 which is inserted into the upper portion of the insertion tube 20 along a longitudinal central axis, and a protrusion 30 with an extended diameter formed at the upper portion of the introduction hole 28.

In addition, it is configured that a spring receiver 32 is formed on the outer circumference of the introduction hole 28, and besides, another threaded portion 34 coupled to the threaded portion 18, which is formed on the outer circumference of the upper portion of the insertion tube 20, is formed on the inner circumference of the spring receiver 32.

It is configured that a second sealing member 38 is inserted into and seated on the protrusion 30 formed in the upper portion of the fastening tube 26, has an incision hole 36 in a circular or "+" shape formed on the top, and is made out of silicon with elasticity, and besides, a spring 40, which performs an elastic action according whether an external force is applied, is inserted into the spring receiver 32 formed on the outer circumference of the fastening tube 26.

According to the present invention, a pressurizing piece 42 which is downwardly pressed by the applied external force and controls opened and closed states of the incision hole 36 in a circular or "+" shape formed in the second sealing member 38 is coupled to the upper portion of the fastening tube 26. A pressurizing hole 44, which maintains a state in which the hole adheres to the circumference of the incision hole 36 in a circular or "+" shape on the second sealing member 38, is formed in the center of the top of the pressurizing piece 42 in a projecting manner, and inclined planes 46 are formed on an edge of the upper end of the pressurizing piece 42 in an outwardly opening manner, wherein an edge of the lower end of the pressurizing piece is coupled to the upper end of the spring 40 in such a manner that the edge and the upper end adhere to each other all the time.

Push buttons 48, which upwardly slide along the inclined planes 46 on the pressurizing piece 42 so as to press the pressurizing piece 42 downwardly when a user pushes the buttons, are mounted on opposing sides of the pressurizing piece 42, respectively, wherein tapered surfaces 50 having the same slope as the inclined planes 46 on the pressurizing piece 42 are formed on the inner circumference of the upper portion of the push buttons 48.

The push buttons 48 are integrally inserted into and coupled to the sides of a body 54 which has another through hole 52 communicating with the pressurizing hole 44 on the pressurizing piece 42 formed in the center.

Besides, according to the present invention, a pivot guiding piece 56 in a disk shape is integrally formed from the middle of the insertion tube 20 in an outwardly projecting manner, wherein the pivot guiding piece 56 is configured to have a saw-toothed portion 58 formed on the outer circumference within a certain range of angles, and a drug guide hole 60, which communicates with the guide hole 14 in the insertion tube 20, formed on one inner side.

In addition, an additional pivot adjusting piece 62 is coupled to the outside of the pivot guiding piece 56 in a covering manner, wherein the pivot adjusting piece 62 has another saw-toothed portion 64, which engages with the saw-toothed portion 58 on the pivot guiding piece 56, formed on the inner circumference, and a drug influx tube 66 formed in a position corresponding to the drug guide hole 60 on the pivot guiding piece 56 in an outwardly projecting manner.

According to the present invention, the drug guide hole 60 on the pivot guide piece 56 is formed in such a manner that the one opening far from the insertion tube is wider, while the other opening close to the insertion tube 20 is narrower in order to correspond to the range of pivoting movement of the drug influx tube 66 on the pivot adjusting piece 62.

Hereinafter, an operation of the present invention is described with reference to FIGS. 1 through 5.

When inserting different catheters 12 such as a tube, a guide wire, or a catheter into a blood vessel at the time of a Cardiac Catheterization or Percutaneous Transluminal Coronary Angioplasty operation, a surgical operator couples an angio needle or the different catheters 12 to a hose connector 16 connected to the lower end of an insertion tube 20, to connect the needle or catheters with a percutaneous artery or a vein. In this state, the surgical operator releases a threaded portion 34 on a fastening tube 26 coupled to another threaded portion 18 formed on the upper portion of the insertion tube 20 so that a through hole 22 on a first sealing member 24 becomes largely expanded, and then pushes push buttons 48 coupled to the outside of the fastening tube 26, so that tapered surfaces 50 of the push buttons 48 move along inclined planes 46 on the pressurizing piece 42, which causes a pressurizing piece 42 to be pushed. As a result, a pressurizing hole 44 on the pressurizing piece 42 presses the periphery of an incision hole 36 in a circular or "+" shape formed on a second sealing member 38, and therefore the incision hole 36 in a circular or "+" shape becomes largely expanded.

After that, when the surgical operator inserts the different catheters 12 into a through hole 52 on a body 54 from outside, an acting force allows tips of the different catheters 12 such as a tube, a guide wire, or a catheter to enter a guide hole 14 in the insertion tube 20 via the incision hole 36 in a circular or "+" shape on the second sealing member 38, an introduction hole 28 on the fastening tube 26, and the through hole 22 on the first sealing member 24, and then the continuous acting force allows the different catheters to be inserted into the coronary artery via a tip of the needle as well as a percutaneous artery or a vein in sequence.

As described above, blood may flow backward while the different catheters 12 are inserted into a percutaneous artery or a vein as well as the coronary artery. Here, it is required to continuously insert the different catheters 12 and prevent the blood flowing backward from leaking to the outside.

This is achieved in such a manner that, when the fastening tube 26 is rotated in a reverse direction, the through hole 22 on the first sealing member 24 becomes gradually narrower by means of a tightening force of the threaded portions 18 and 34 on the insertion tube 20 and the fastening tube 26.

In case of the second sealing member 38, when the pressurizing piece 42 downwardly moves by means of an action of the push buttons 48, a spring 40 is compressed, while, when a force applied to the push buttons 48 is removed, the pressurizing piece 42 and the pressurizing hole 44 move upwardly by means of a restoring force of the spring 40 and the tapered surfaces 50 on the push buttons 48 downwardly move along the inclined planes 46 on the pressurizing piece 42, and therefore, the incision hole 36 in a circular or "+" shape on the second sealing member 38 returns a closed state.

Accordingly, the blood flowing backward is clearly shut off by the first and second sealing members 24 and 38 when the different catheters 12 are inserted.

Besides, it is required to inject a medicine such as a thrombolitic drug as necessary during a Cardiac Catheterization or Percutaneous Transluminal Coronary Angioplasty operation. Here, a hose for supplying the medicine is inserted into a drug influx tube 66 formed on a pivot adjusting piece 62.

Herein, the medicine such as a thrombolitic drug is injected into the guide hole 14 in the insertion tube 20 via the drug influx tube 66 and a drug guide hole 60 formed in the pivot guiding piece 56, and then reaches a desired position in the coronary artery via a percutaneous artery or a vein.

As described above, in the course of injecting a medicine, when angles of the drug influx tube 66 are adjusted on a basis of body conditions or movements of a patient, pivoting the pivot adjusting piece 62 to the left or the right allows the drug influx tube 66 to be pivoted in a stepwise manner in a state in which a saw-toothed portion 64 formed on the inner circumference of the pivot adjusting piece 62 engages with another saw-toothed portion 58 formed the outer circumference of the pivot guiding piece 56, so that angles of the tube vary.

Accordingly, injecting a medicine may be conveniently and efficiently performed at the time of a Cardiac Catheterization or Percutaneous Transluminal Coronary Angioplasty operation.

According to the present invention, a hemostasis valve device which allows a tube, a guide wire, or a catheter to be inserted into the left or right coronary artery via the femoral artery or an arm artery at the time of a Cardiac Catheterization or Percutaneous Transluminal Coronary Angioplasty operation, wherein two sealing members are mounted in two independent positions, and the sealing members are opened and closed by means of press and release actions of push buttons coupled to the outside of a fastening tube as well as the rotation of the fastening tube, respectively, has an effect that the leakage of blood or the inflow of outside air is simply and clearly shut off during the operation.

According to the present invention, the hemostasis valve device also has another effect that a drug influx tube for allowing a medicine such as a thrombolitic drug to flow into a patient during the Cardiac Catheterization or Percutaneous Transluminal Coronary Angioplasty operation pivots and is adjusted in a stepwise manner within a certain range of angles on a basis of body conditions or movements of the patient, so that the convenience and efficiency of the surgical operation is more improved.

The invention claimed is:

1. Hemostasis valve device comprising:
    an insertion tube which has a guide hole into which different catheters such as a tube, a guide wire, or a catheter are inserted along a longitudinal central axis formed inside in a penetrating manner, has a hose connector connected to a hose into which a needle or a catheter is inserted coupled to a lower portion of the insertion tube, and has a threaded portion formed on the outer circumference of an upper portion of the insertion tube;

an elastic first sealing member which is inserted into and seated in the upper portion of the insertion tube, and has a through hole formed along a longitudinal central axis;

a fastening tube which has an introduction hole inserted into the upper portion of the insertion tube along a longitudinal central axis formed inside, has a protrusion with an extended diameter formed at an upper portion of the introduction hole, has a spring receiver formed on the outer circumference of the introduction hole, and has another threaded portion engaging with the threaded portion, which is formed on the outer circumference of the upper portion of the insertion tube, formed on the inner circumference of the spring receiver;

an elastic second sealing member which is inserted into and seated on the protrusion formed in an upper portion of the fastening tube, and has an incision hole in a circular or "+" shape formed on the top;

a spring which is inserted into the spring receiver formed on the outer circumference of the fastening tube, and performs an elastic action according to whether an external force is applied;

a pressurizing piece which has a pressurizing hole formed in the center of a top of the pressurizing piece in a projecting manner in order to maintain a state in which the hole adheres to the circumference of the incision hole in a circular or "+" shape on the second sealing member, has inclined planes formed on an edge of the upper portion in an outwardly opening manner, and is mounted in a state in which an edge of the lower end adheres to an upper end of the spring all the time;

push buttons which are mounted on opposing sides of the pressurizing piece, and upwardly slide along the inclined planes on the pressurizing piece so as to press the pressurizing piece downwardly when a user pushes the buttons in a state in which tapered surfaces having a same slope as the inclined planes on the pressurizing piece are formed on the inner circumference of an upper portion of the buttons; and a body which allows the push buttons to be inserted into and coupled to the body, and has another through hole, which communicates with the pressurizing hole on the pressurizing piece, formed in the center.

2. The hemostasis valve device according to claim 1, characterized in that the device comprises a pivot guiding piece which is formed in a middle of the insertion tube in an outwardly projecting manner and a disk shape, has a saw-toothed portion formed on the outer circumference within a certain range of angles, and has a drug guide hole, which communicates with the guide hole in the insertion tube, formed on one inner side, and a pivot adjusting piece which is coupled to the outside of the pivot guiding piece in a covering manner, has another saw-toothed portion formed on the inner circumference corresponding to the saw-toothed portion on the pivot guiding piece so that the two saw-toothed portions engage with each other, and has a drug influx tube formed in a position corresponding to the drug guide hole on the pivot guiding piece.

3. The hemostasis valve device according to claim 2, characterized in that the drug guide hole on the pivot guiding piece is formed in such a manner that one opening far from the insertion tube is wider, while another opening close to the insertion tube is narrower in order to correspond to the range of pivoting movements of the drug influx tube on the pivot adjusting piece.

* * * * *